(12) United States Patent
Sweeney et al.

(10) Patent No.: US 9,901,681 B2
(45) Date of Patent: Feb. 27, 2018

(54) MEDICAL INJECTOR WITH SLIDABLE SLEEVE ACTIVATION

(75) Inventors: Matthew D. Sweeney, Bloomfield, NJ (US); Richard A. Cronenberg, Mahwah, NJ (US); Lionel Vedrine, Palo Alto, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 350 days.

(21) Appl. No.: 13/063,792

(22) PCT Filed: Sep. 18, 2009

(86) PCT No.: PCT/US2009/057595
§ 371 (c)(1),
(2), (4) Date: May 19, 2011

(87) PCT Pub. No.: WO2010/033882
PCT Pub. Date: Mar. 25, 2010

(65) Prior Publication Data
US 2011/0213315 A1    Sep. 1, 2011

Related U.S. Application Data

(60) Provisional application No. 61/192,464, filed on Sep. 18, 2008.

(51) Int. Cl.
*A61M 5/24* (2006.01)
*A61M 5/20* (2006.01)
(Continued)

(52) U.S. Cl.
CPC ......... *A61M 5/2448* (2013.01); *A61M 5/2033* (2013.01); *A61M 5/3146* (2013.01);
(Continued)

(58) Field of Classification Search
CPC .............. A61M 5/326; A61M 5/31578; A61M 5/31576; A61M 5/2033; A61M 5/1458;
(Continued)

(56) References Cited

U.S. PATENT DOCUMENTS 2,816,543 A * 12/1957 Scherer .................. A61M 5/30
604/68
3,605,744 A * 9/1971 Dwyer ................ A61M 5/2033
604/139
(Continued)

FOREIGN PATENT DOCUMENTS

EP       1743666 A1    1/2007
WO    2005070481 A1    8/2005
WO    2008027382 A2    3/2008

*Primary Examiner* — Bhisma Mehta
*Assistant Examiner* — Matthew A Engel
(74) *Attorney, Agent, or Firm* — The Webb Law Firm (57) ABSTRACT

In one aspect, a medical injector is provided herein which includes a body; a displaceable plunger disposed in the body; a spring disposed to advance the plunger; a releasable retainer for retaining the plunger in a first state against force of the spring; and, a sleeve disposed on the body, the sleeve being slidable relative to the body. Sliding movement of the sleeve over a predetermined extent relative to the body results in the releasable retainer releasing the plunger thereby allowing the spring to advance the plunger. Advantageously, the subject invention provides a medical injector having an automated plunger drive which is triggered upon sliding movement of the sleeve, thereby minimizing premature or failed activations.

8 Claims, 7 Drawing Sheets

(51) Int. Cl.
  *A61M 5/31* (2006.01)
  *A61M 5/315* (2006.01)

(52) U.S. Cl.
  CPC ....... *A61M 5/3156* (2013.01); *A61M 5/31553* (2013.01); *A61M 2005/2073* (2013.01); *A61M 2005/2451* (2013.01)

(58) Field of Classification Search
  CPC .. A61M 2005/3217; A61M 2005/3206; A61M 5/31581; A61M 5/208
  USPC .......... 604/68, 110, 136, 197, 218, 224, 211
  See application file for complete search history.

(56) References Cited

U.S. PATENT DOCUMENTS

| | | | | |
|---|---|---|---|---|
| 3,712,301 A * | 1/1973 | Sarnoff | A61M 5/2033 | 604/136 |
| 3,882,863 A * | 5/1975 | Sarnoff | A61M 5/2033 | 604/136 |
| 4,498,904 A * | 2/1985 | Turner | A61M 5/24 | 422/928 |
| 4,596,556 A * | 6/1986 | Morrow | A61M 5/30 | 604/70 |
| 4,678,461 A * | 7/1987 | Mesa | A61M 5/2033 | 604/157 |
| 4,710,178 A * | 12/1987 | Henri | A61M 5/31581 | 401/181 |
| 4,755,169 A * | 7/1988 | Sarnoff | A61M 5/2066 | 604/136 |
| 5,085,642 A * | 2/1992 | Sarnoff | A61M 5/2033 | 604/134 |
| 5,092,842 A * | 3/1992 | Bechtold | A61M 5/20 | 604/135 |
| 5,295,976 A * | 3/1994 | Harris | A61M 5/31551 | 604/208 |
| 5,300,041 A * | 4/1994 | Haber | A61M 5/24 | 604/207 |
| 5,304,152 A * | 4/1994 | Sams | A61M 5/31553 | 604/207 |
| 5,383,851 A * | 1/1995 | McKinnon et al. | | 604/68 |
| 5,478,316 A * | 12/1995 | Bitdinger | A61M 5/2033 | 604/134 |
| 5,503,627 A * | 4/1996 | McKinnon | A61M 5/24 | 604/68 |
| 5,514,097 A * | 5/1996 | Knauer | A61M 5/20 | 604/136 |
| 5,536,249 A * | 7/1996 | Castellano | G06F 19/3468 | 128/DIG. 1 |
| 5,545,147 A * | 8/1996 | Harris | A61M 5/31551 | 604/208 |
| 5,569,189 A * | 10/1996 | Parsons | A61M 5/1782 | 604/22 |
| 5,599,309 A * | 2/1997 | Marshall | A61M 5/2033 | 604/117 |
| 5,679,111 A * | 10/1997 | Hjertman | A61M 5/20 | 604/135 |
| 5,865,795 A * | 2/1999 | Schiff | A61M 5/30 | 604/68 |
| 5,891,086 A * | 4/1999 | Weston | A61M 5/30 | 604/143 |
| 6,221,053 B1 * | 4/2001 | Walters | A61M 5/31551 | 604/208 |
| 6,241,709 B1 * | 6/2001 | Bechtold | A61M 5/2033 | 604/207 |
| 6,454,743 B1 * | 9/2002 | Weber | A61M 5/2033 | 604/131 |
| 6,506,177 B2 * | 1/2003 | Landau | A61M 5/30 | 604/135 |
| 6,544,234 B1 * | 4/2003 | Gabriel | A61M 5/2033 | 604/134 |
| 6,793,646 B1 * | 9/2004 | Giambattista | A61M 5/2066 | 604/208 |
| 6,976,976 B2 * | 12/2005 | Doyle | A61M 5/3137 | 128/919 |
| 7,156,823 B2 * | 1/2007 | Landau | A61M 5/30 | 604/110 |
| 7,195,616 B2 * | 3/2007 | Diller | A61M 5/31566 | 604/207 |
| 7,361,160 B2 * | 4/2008 | Hommann | A61M 5/2033 | 604/198 |
| 7,645,265 B2 * | 1/2010 | Stamp | A61M 5/2033 | 604/134 |
| 7,678,084 B2 * | 3/2010 | Judson | A61M 5/24 | 604/110 |
| 7,699,802 B2 * | 4/2010 | Steinway | A61M 5/24 | 604/131 |
| 7,901,377 B1 * | 3/2011 | Harrison | A61M 5/2033 | 604/156 |
| 7,967,010 B2 * | 6/2011 | Vedrine | A61M 5/2429 | 128/200.14 |
| 8,075,517 B2 * | 12/2011 | Karlsson | A61M 5/20 | 604/134 |
| RE43,834 E * | 11/2012 | Steenfeldt-Jensen | A61M 5/31551 | 604/207 |
| 8,672,883 B2 * | 3/2014 | Denning | A61M 5/2429 | 604/110 |
| 9,675,757 B2 * | 6/2017 | Harrison | A61M 5/2033 | |
| 2001/0005781 A1 * | 6/2001 | Bergens | A61M 5/2033 | 604/208 |
| 2002/0032412 A1 * | 3/2002 | Riemelmoser | A61M 5/326 | 604/197 |
| 2002/0095120 A1 * | 7/2002 | Larsen | A61M 5/2033 | 604/187 |
| 2004/0133163 A1 * | 7/2004 | Schiffmann | A61M 5/30 | 604/131 |
| 2004/0225262 A1 * | 11/2004 | Fathallah | A61M 5/2033 | 604/198 |
| 2004/0236285 A1 * | 11/2004 | Fisher | A61M 5/3158 | 604/207 |
| 2005/0027255 A1 * | 2/2005 | Lavi | A61M 5/2033 | 604/135 |
| 2005/0101919 A1 | 5/2005 | Brunnberg | | |
| 2005/0277896 A1 * | 12/2005 | Messerli | A61M 5/344 | 604/240 |
| 2006/0089593 A1 * | 4/2006 | Landau | A61M 5/30 | 604/68 |
| 2006/0089594 A1 * | 4/2006 | Landau | A61M 5/2033 | 604/68 |
| 2006/0153693 A1 * | 7/2006 | Fiechter | A61M 5/31553 | 417/63 |
| 2006/0189931 A1 | 8/2006 | Riemelmoser | | |
| 2006/0229569 A1 * | 10/2006 | Lavi | A61M 5/326 | 604/197 |
| 2006/0229570 A1 | 10/2006 | Lovell et al. | | |
| 2006/0270985 A1 * | 11/2006 | Hommann | A61M 5/2033 | 604/136 |
| 2007/0021715 A1 * | 1/2007 | Kohlbrenner | A61M 5/20 | 604/67 |
| 2008/0147006 A1 | 6/2008 | Brunnberg et al. | | |
| 2009/0234297 A1 * | 9/2009 | Jennings | A61M 5/2033 | 604/195 |
| 2009/0254044 A1 * | 10/2009 | Kohlbrenner | A61M 5/20 | 604/207 |
| 2009/0275916 A1 * | 11/2009 | Harms | A61M 5/24 | 604/506 |
| 2013/0310757 A1 * | 11/2013 | Brereton | A61M 5/3158 | 604/197 |
| 2016/0038678 A1 * | 2/2016 | Kemp | A61M 5/2033 | 604/506 |

* cited by examiner

MEDICAL INJECTOR WITH SLIDABLE SLEEVE ACTIVATION

FIELD OF THE INVENTION

This invention relates to medical injectors, and, more particularly, to medical injectors having plunger drive mechanisms.

BACKGROUND OF THE INVENTION

Medical injectors are well known in the prior art, including injectors which have internal drive mechanisms for plunger advancement. Plunger advancement may be utilized to conduct automated reconstitution of a two-or more part medicament and/or to cause automated injection. More specifically, the automation of plunger advancement may be utilized to cause combination of a multiple part (e.g., wet/dry) medicament. In addition, or alternatively, the automated advancement of the plunger may cause a needle to be advanced for injection and/or medicament to be driven through the needle during injection. Such automated action requires a trigger mechanism. Concerns exist over premature or failed trigger activation.

SUMMARY OF THE INVENTION

In one aspect, a medical injector is provided herein which includes a body; a displaceable plunger disposed in the body; a spring disposed to advance the plunger; a releasable retainer for retaining the plunger in a first state against force of the spring; and, a sleeve disposed on the body, the sleeve being slidable relative to the body. Sliding movement of the sleeve over a predetermined extent relative to the body results in the releasable retainer releasing the plunger thereby allowing the spring to advance the plunger. Advantageously, the subject invention provides a medical injector having an automated plunger drive which is triggered upon sliding movement of the sleeve, thereby minimizing premature or failed activations.

In a further aspect, a medical injector is provided herein which includes a body; a displaceable plunger disposed in the body, the plunger having at least one thread formed thereon; a stem disposed in the body, the stem having at least one thread formed thereon; a button fixed to the stem; a spring disposed to advance the button away from the body; and, a releasable retainer for releasably retaining the button against force of the spring. Upon a predetermined extent of relative movement between the plunger and the stem, the thread of the plunger threadably engages the thread of the stem such that the stem rotates, rotation of the stem causing the releasable retainer to release the button thereby allowing the spring to advance the button. Advantageously, the subject invention provides a medical injector with a fixed order of operation, whereby access to a plunger drive button is only provided at a desired phase of operation.

These and other features of the subject invention will be better understood through a study of the following detailed description and accompanying drawings.

BRIEF DESCRIPTION OF THE DRAWINGS

FIG. 14 shows a stem useable with the subject invention; and.

DETAILED DESCRIPTION OF THE INVENTION

With reference to the figures, a medical injector is shown and generally designated with the reference numeral 10. The medical injector 10 may be of various types, but preferably is of the pen injector type. The medical injector 10 may be used to administer various injectable liquids, particularly medicaments.

Figure 1:
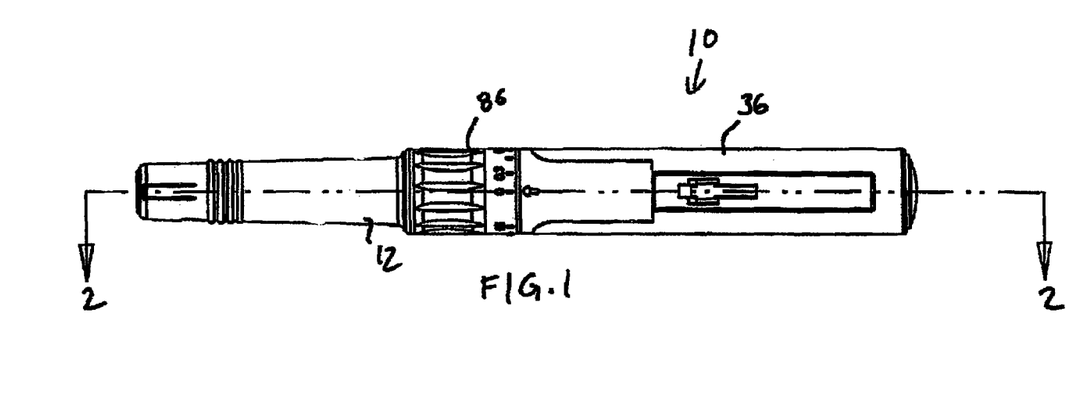
FIG. 1 shows a medical injector formed in accordance with the subject invention.
Figure 2:
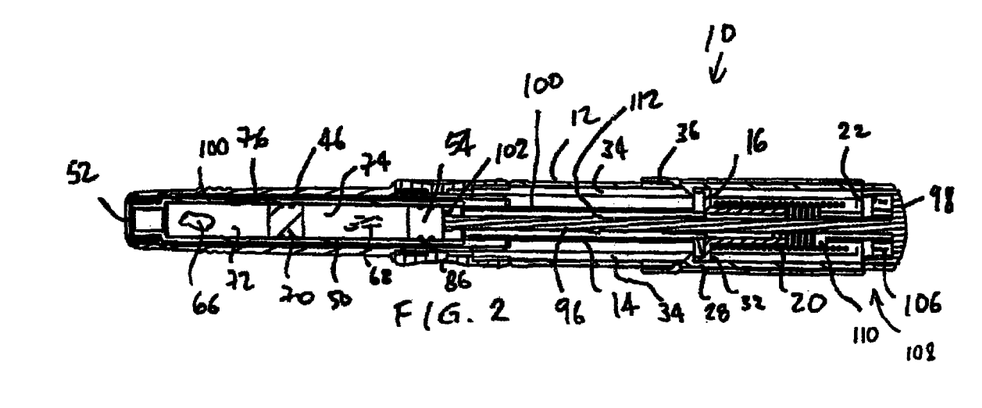
FIG. 2 is a cross-sectional view taken along line 2-2 of FIG. 1.
Figure 3:
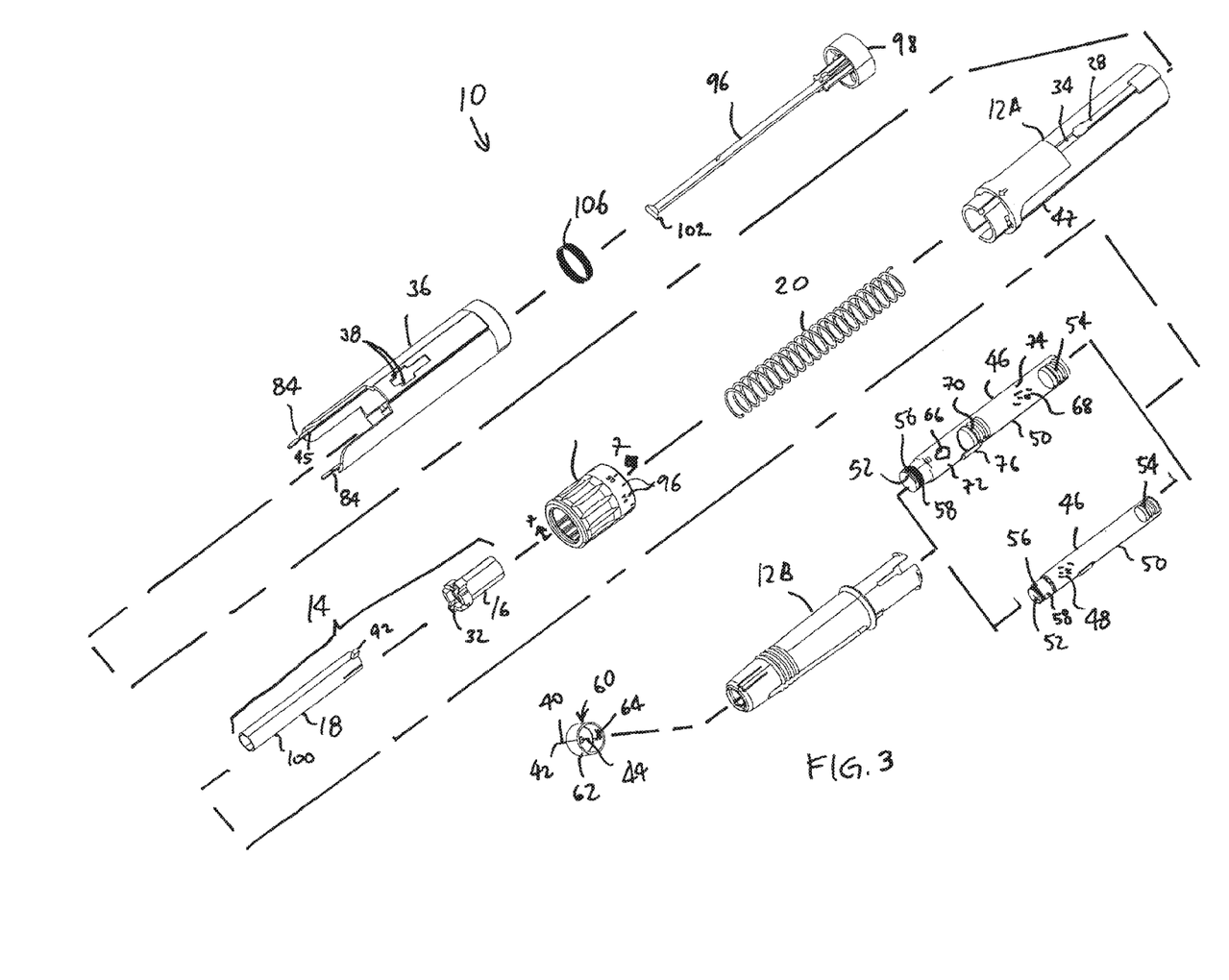
FIG. 3 is an exploded view of a medical injector formed in accordance with the subject invention.

As shown in FIG. 2, the medical injector 10 includes a body 12 having an axially-displaceable plunger 14 disposed therein. With reference to FIG. 3, the body 12 may be formed of multiple components, such as body portions 12A, 12B. The plunger 14 preferably includes a first plunger portion 16 and a second plunger portion 18. The plunger 14 may be formed as a single piece or by modular components, such as the first and second plunger portions 16, 18 being separate components. Where dose setting is utilized, as described below, the first and second plunger portions 16, 18 are formed separately.

A spring 20 is also provided configured and positioned to advance the plunger 14 a predetermined distance. Preferably, the spring 20 is a compression or coil spring, but other biasing elements may likewise be utilized. Preferably, the spring 20 is disposed between a cross-piece 22 formed on a proximal end 12a of the body 12 and the plunger 14, particularly, the first plunger portion 16. A shoulder 24 may be formed on the plunger 14 against which the spring 20 applies force.

Figure 5:
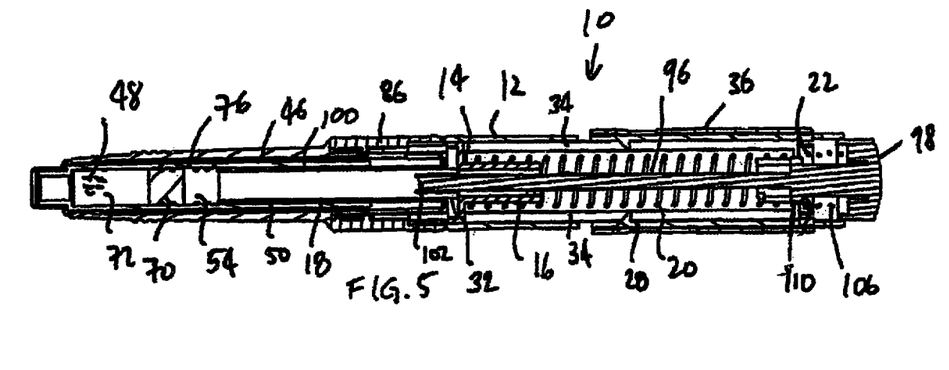
FIGS. 5 and 6 are cross-sectional views showing the medical injector of FIG. 1 in post-reconstitution and needle mounted states, respectively.

A releasable retainer 26 is provided which is configured and positioned to releasably retain the plunger 14 in an initial first state against the force of the spring 20. The first state of the plunger 14 is shown in FIG. 2. The releasable retainer 26 is configured such that, upon activation, the releasable retainer 26 releases the plunger 14 thereby allowing the spring 20 to advance the plunger 14, as shown in FIG. 5.

It is preferred that the plunger 14 be advanced in a distal direction. As used herein, distal refers to a direction towards a patient during use, while proximal refers to a direction away from a patient during use.

Figure 4:
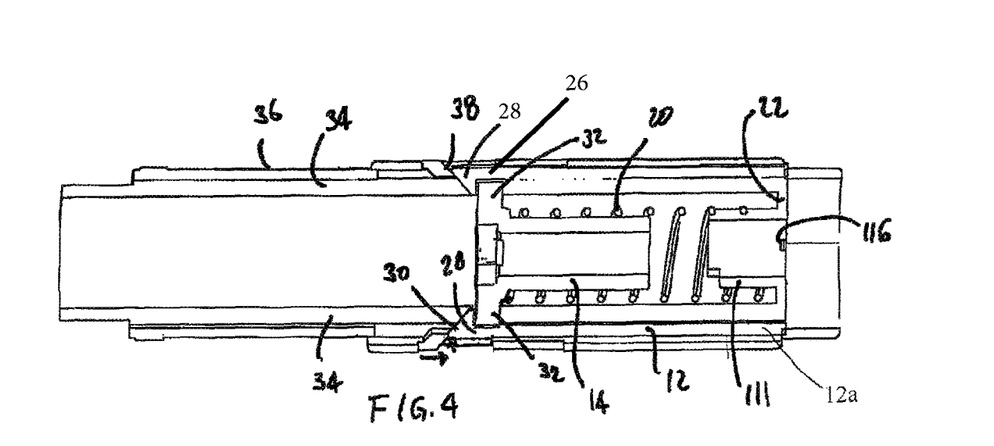
FIG. 4 is a schematic of a releasable retaining arrangement useable with the subject invention.

By way of non-limiting example, and with reference to FIG. 4, the releasable retainer 26 may include one or more deflectable locking arms 28 formed on the body 12. The locking arms 28 each include a detent 30 formed to interferingly engage a portion of the plunger 14, particularly the first plunger portion 16, in retaining the plunger 14 in an initial first state prior to use. Preferably, the first plunger portion 16 includes one or more wings 32 which extend radially outwardly from the plunger 14. The detents 30 are formed to interferingly engage the wings 32, as shown in FIG. 4.

The wings 32 are formed to slide along guide channels 34 formed in the body 12. The guide channels 34 limit the wings 32 to straight-line motion. Thus, the first plunger portion 16 is maintained non-rotatable relative to the body 12. Preferably, the locking arms 28 are axially aligned with the guide channels 34. Accordingly, the guide channels 34 maintain the wings 32 in axial alignment with the locking arms 20.

To facilitate release of the plunger 14 from the releasable retainer 26, a sleeve 36 is provided, the sleeve 36 being disposed on the body 12 formed for sliding movement relative thereto. The sleeve 36 preferably is located exteriorly of the body 12 for easy handling. The sleeve 36 includes one or more ramped activation surfaces 38 which are preferably tapered to face proximally and outwardly from the body 12.

In an initial state, the activation surfaces 38 are spaced from the detents 30. To release the plunger 14, the sleeve 36 is slid proximally relative to the body 12 with the activation surfaces 38 engaging the detents 30. With sufficient proximal movement, the activation surfaces cause outward deflection of the detents 30 and, thus, release of the plunger 14 from the first state. Upon release, the plunger 14 is advanced distally under force of movement of the spring 20 with the wings 32 sliding along the guide channels 34. The sleeve 36 and/or the body 14 may include a rib 45 formed to engage a cooperating channel 47 so as to limit relative rotation therebetween. In this manner, axial alignment of the activation surfaces 38 with the locking arms 28 may be maintained.

The medical injector 10 includes a reservoir 46 disposed in the body 12 formed to accommodate medicament or other substance 48 for injection into a patient. As shown in FIG. 3, the reservoir 46 may be a single chamber disposed in a barrel 50 sealed at a proximal end by a septum 52 and sealed at a distal end by a stopper 54 which is formed to be slidable through the barrel 50 for urging the substance 48 therefrom, as known in the art. The medical injector 10 also includes a needle mounting surface 56 having features 58 formed thereon for mounting a needle 60 thereto. The needle 60 may include a hub 62 having mounting features 64 provided thereon for cooperative engagement with the features 58 in mounting the needle 60 to the needle mounting surface 56. The features 58 and the mounting features 64 may be of any known cooperating elements which permit a mechanical connection therebetween, such as threads or bayonet lock, and/or a frictional interengagement, such as a Luer mounting. The needle mounting surface 56 may be formed on the first body portion 12 or a component thereof.

The needle 60 also includes a needle cannula 40 having a distal end 42, formed for insertion into a patient, and a proximal end 44.

The reservoir 46 may be configured to accommodate multiple components which are mixable for reconstitution. For example, as shown in FIG. 2, the reservoir 46 may accommodate first and second mixable components 66, 68. The stopper 54 may be associated with the reservoir 46 such that distal advancement of the stopper 54 over a predetermined distance shall cause mixing of the first and second mixable components 66, 68. Any known arrangement for allowing such mixing may be utilized. By way of non-limiting example, the first and second mixable components 66, 68 may be separated by a secondary stopper 70. The secondary stopper 70 divides the reservoir 46 into first and second chambers 72, 74, respectively, accommodating the first and second mixable components 66, 68. The septum 52 seals off the distal end of the first chamber 72, while the stopper 54 is positioned to seal off the proximal end of the second chamber 74. Preferably, if a dry component is used as one of the mixable components, the dry mixable component is located in the first chamber 72.

One or more by-pass channels 76 are formed in the wall of the reservoir 46. In an initial state, as shown in FIG. 2, the secondary stopper 70 is located at least partially proximally of the by-pass channels 76 so as to define a seal between the first and second chambers 72, 74 and to define a seal between the second chamber 74 and the by-pass channels 76. With distal advancement of the stopper 54, and with the second mixable component 68 being wet and generally incompressible, force of movement of the stopper 54 is transmitted to the secondary stopper 70 through the second mixable component 68. With sufficient distal movement of the secondary stopper 70, the second chamber 74 comes into communication with the by-pass channels 76, thus allowing the second mixable component 68 to be urged into the first chamber 72 with further distal movement of the stopper 54. With sufficient distal advancement of the stopper 54, the second chamber 74 is collapsed with none or substantially none of the second mixable component 68 remaining therein, as shown in FIG. 5. In addition, the secondary stopper 70 is located so as to define a seal between the first chamber 72 and the by-pass channels 76. The first and second mixable components 66, 68 are mixed within the first chamber 72, such as through agitation of the medical injector 10, so as to produce the injectable substance 48, ready for injection.

The barrel 50 of the reservoir 46 may be the barrel of a separate drug cartridge, as shown in the figures, or a portion of the medical injector 10, particularly the body 12.

As will be recognized by those skilled in the art, other arrangements for permitting reconstitution may be utilized. In addition, more than two-part systems, such as three-part and so forth, systems may be utilized. Active medical ingredients may be included in one or both of the first and second mixable components 66, 68. The first mixable component 66 may be dry (e.g., a powder or granular substance) and/or a liquid (e.g., flowable (slurry or liquid)). As mentioned above, the second mixable component 70 is preferably only a wet flowable component, such as a liquid or slurry.

Distal advancement of the plunger 14 under force of the spring 20 may be used to achieve one or more objectives. The plunger 14 is configured to act against the stopper 54 and cause displacement thereof. With the reservoir 46 being configured for reconstitution, autoreconstitution of the contents of the reservoir 46 may be achieved. In addition, or alternatively, the medical injector 10 may be configured to be an autoinjector, where the needle 60 is initially housed within the body 12 and forced thereout of under force of the spring 20 so as to pierce a patient's skin, e.g., with forward movement of the reservoir 46, as known in the art. In addition, or alternatively, distal advancement of the plunger 14 may cause administration of the contents of the reservoir 46 through the injected needle.

Depending on the desired effect, the medical injector 10 may be configured to have the plunger 14 be driven a predetermined distance. A physical stop, such as interengagement between the wings 32 and a proximal end 78 of the reservoir 46 (e.g., proximal end of the barrel 50) or a portion of the body 12 or another component (such as the dose knob described below), may be employed to limit distal advancement of the plunger 14. Under certain circumstances, as shown in FIG. 5, the plunger 14 may be distally advanced without the needle 60 being mounted to the medical injector 10. Thus, the reservoir 46 is not vented during such action. With the needle 60 being subsequently mounted to the reservoir 46 (FIG. 6), any residual gases trapped in the reservoir 46 are purged through the needle 60. It may be preferred to not provide a physical stop to the distal advancement of the plunger 14. In this manner, the contents of the reservoir 46 may be maximally compressed under force of the spring 20. With subsequent mounting of the needle 60 onto the medical injector 10, the reservoir 46 is vented thus permitting further distal advancement of the plunger 14. This secondary distal advancement may assist in priming the needle 60 for use.

Figure 7:
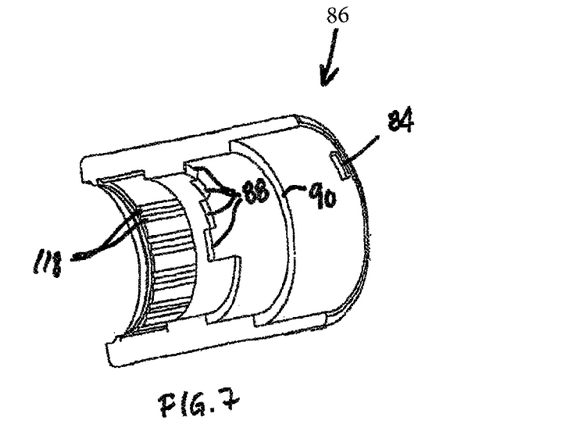
FIG. 7 is a cross-sectional view of the dose knob taken along line 7-7 of FIG. 3.
Figures 8, 9:
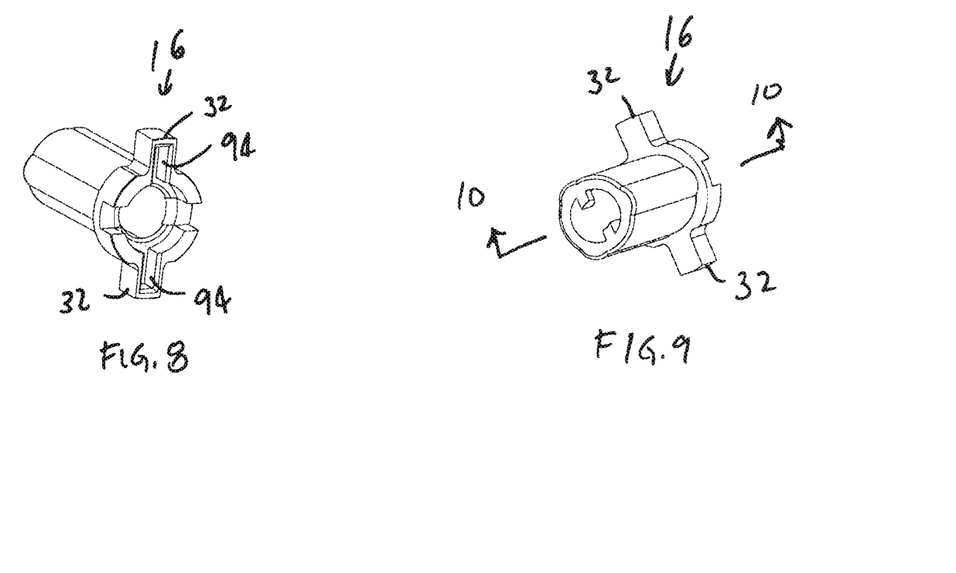
FIGS. 8-10 show a first plunger portion useable with the subject invention.
Figure 10:
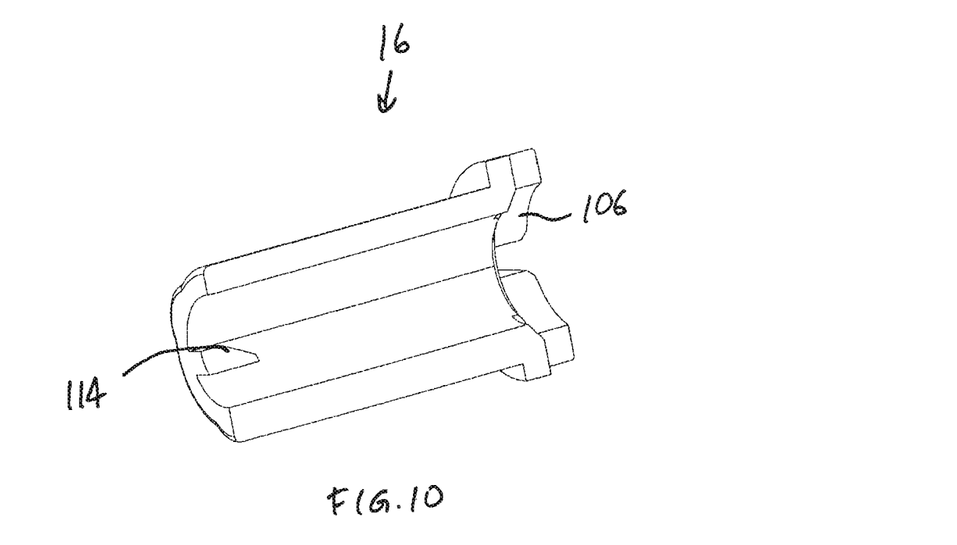
Figure 11:
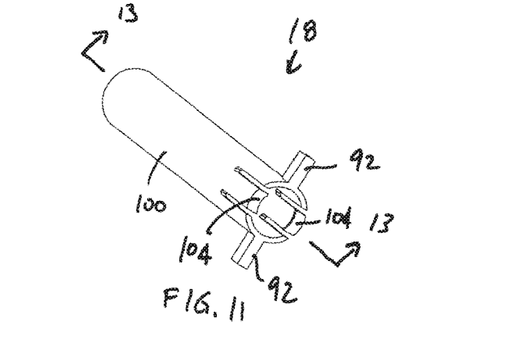
FIGS. 11-13 show a second plunger portion useable with the subject invention.
Figure 12:
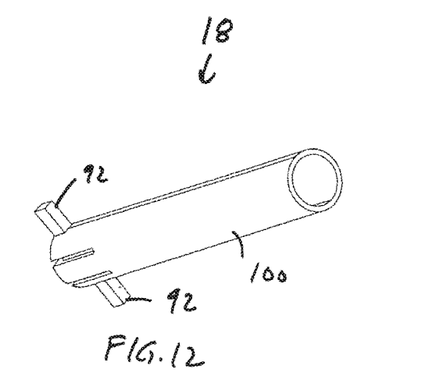
Figure 13:
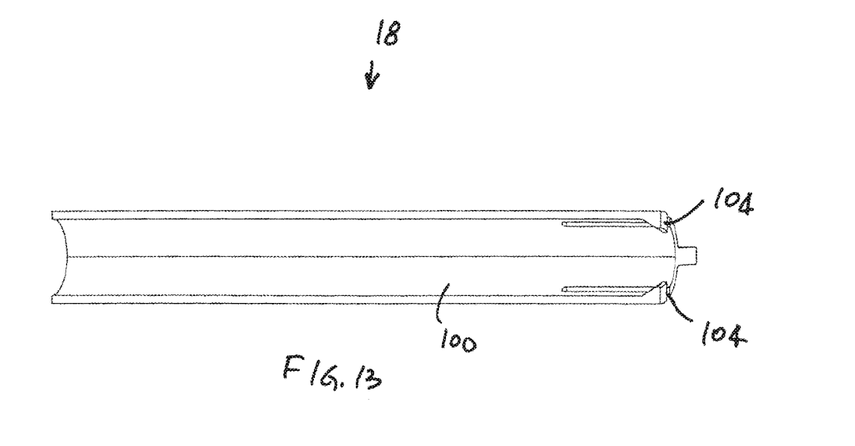
Figure 14:
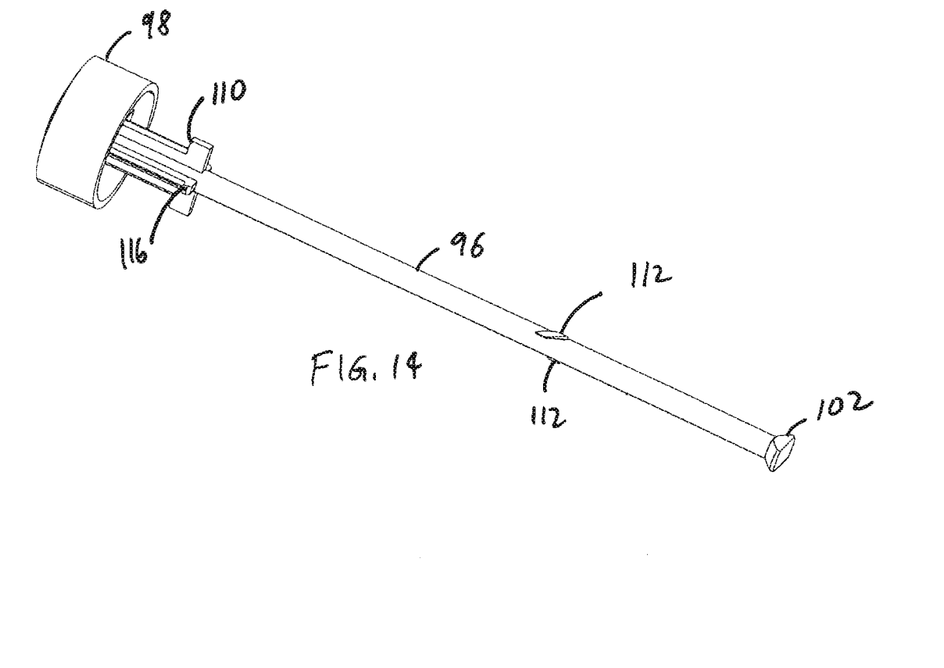

To prevent inadvertent activation of the plunger 14, a locking ring 80 may be rotatably disposed on the body 12 having one or more protrusions 82 extending radially inwardly therefrom (FIG. 7). One or more notches 84 (FIG. 3), corresponding to the protrusions 82, may be formed on the sleeve 36. In an initial state, the protrusions 82 are located in the notches 84 so as to prevent sliding movement of the sleeve 36 relative to the body 12. Radial displacement of the locking ring 80 frees the notches 84 and, thus, permits sliding movement of the sleeve 36, particularly proximal sliding movement.

For dose setting, the locking ring 80 may be configured as a dose knob 86. As shown in FIG. 7, the dose knob 86 includes a plurality of axially and radially spaced apart abutment surfaces 88 which represent different dose amounts. In addition, the dose knob 86 includes one or more stop ledges 90 corresponding to the wings 32. The stop ledges 90 are configured to interferingly engage the wings 32 so as to limit distal advancement thereof. The stop ledges 90 are axially aligned with the guide channels 34 in all radial positions of the dose knob 86.

With dose setting, the first and second plunger portions 16, 18 are formed separately. The second plunger portion 18 is formed with tabs 92 formed to nest within pockets 94 formed in the wings 32. With this arrangement, the first and second plunger portions 16, 18 move in concert under force of movement of the spring 20. The tabs 92, however, are formed to by-pass the stop ledges 90 so as to engage one of the abutment surfaces 88.

In use, the dose knob 86 is turned about the body 12 to select a dose. Indicia 96 may be provided on the dose knob 86 and/or the body 12 to indicate dosage settings. With dose setting, the abutment surfaces 88 corresponding to the selected dose amount are axially aligned with the tabs 92. With release of the plunger 14 from the first state as described above, the first and second plunger portions 14, 16 are distally advanced under force of movement of the spring 20. With eventual distal movement, the wings 32 engage the stop ledges 90, thus being stopped from further distal advancement. With the spring 20 acting against the first plunger portion 16, and the first plunger portion 16 being stopped from further distal movement, the second plunger portion 18 also stops at the same location.

The second plunger portion 18 may be distally advanced separately from the first plunger portion 16 to engage the stopper 54 and cause distal advancement thereof. The movement of the stopper 54 causes administration of the injectable solution 48. The selected abutment surfaces 88 limit the distal advancement and thus control dosage amount.

Movement of the plunger 14 from the first state may cause movement of the stopper 54 and autoreconstitution of the first and second mixable components 66, 68. Preferably, the stroke of the plunger 14 is selected to cause full autoreconstitution prior to the wings 32 engaging the stop ledges 90. It is preferred that autoreconstitution be conducted without the needle 60 being mounted to the medical injector 10. Thus, the reservoir 46 is not vented during autoreconstitution. As discussed above, the mounting of the needle 60 causes venting and purging of any trapped gases. Purging of trapped gases causes reduction in the volume entrapped in the reservoir. Reduction in volume permits the spring 20 to cause secondary distal advancement of the plunger 14. It is preferred that the wings 32 engage the stop ledges 90 upon the secondary distal advancement of the plunger 14.

Figure 6:
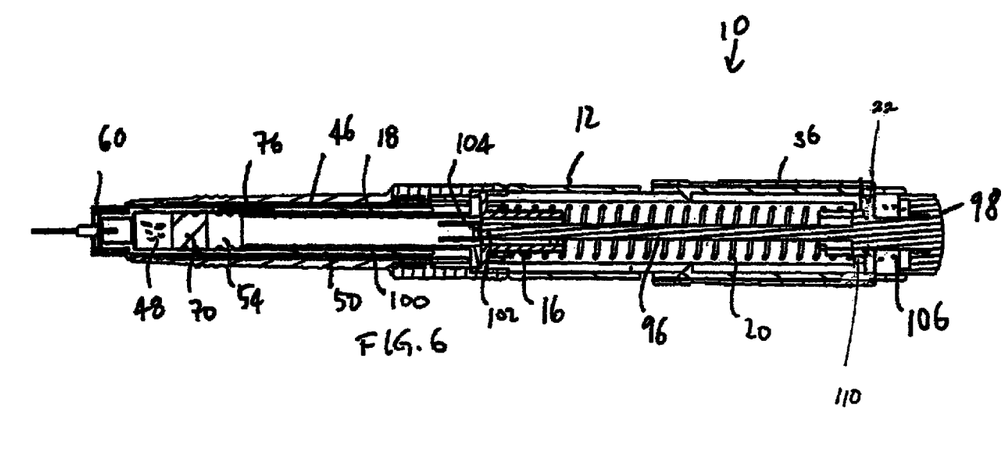

For dosage administration, the second plunger portion 18 may be advanced by stem 96 which is affixed to button 98. The button 98 is accessible by a user to receive force for causing manual dose administration. The stem 96 may extend through the first plunger portion 16 to engage the second plunger portion 18 and cause movement thereof under force of movement of the button 98. More particularly, as shown in FIG. 2, the stem 96 extends into tubular portion 100 of the second plunger portion 18 in the initial first state of the plunger 14. The tubular portion 100 is sized to engage the stopper 54 and cause distal advancement thereof. In addition, the stem 96 has an enlarged head 102. With distal movement of the second plunger portion 18 during autoreconstitution, the tubular portion 100 is sized to slide past the enlarged head 102, as shown in FIG. 5. Inwardly extending tangs 104 are located at or in proximity to the proximal end of the tubular portion 100. The tangs 104 are formed to by-pass the enlarged head 102 with sufficient distal movement of the second plunger portion 18 (FIG. 6). Once by-passed, the tangs 104 are located to interferingly engage the enlarged head 102 with subsequent distal movement of the stem 96 relative to the second plunger portion 18. Thus, distal displacement of the stem 96, via force applied to the button 98, is transmitted to the second plunger portion 18. In turn, the second plunger portion 18 advances distally separately from the first plunger portion 16 which is stopped by the stop ledges 90. The second plunger portion 18 advances the stopper 54 in causing dose administration. The length of stroke of movement of the second plunger portion 18 is defined by the distance the tabs 92 travel to interengage the selected abutment surfaces 88. The greater the distance tabs 92 travel before engaging the selected abutment surfaces 88, the greater the administered dose; conversely, the smaller the distance, the smaller the dose.

The first plunger portion 16 may be formed with recess 106 at a distal end thereof to provide clearance to accommodate the enlarged head 102 prior to distal advancement of the stem 96.

The medical injector 10 may be of various types, including fixed dose or variable dose. Preferably, the medical injector 10 is a single, variable dose, autoreconstitution device. In addition, it is preferred that the medical injector 10 be configured to have a fixed order of operation: dose setting; autoreconstitution; and, manual drug administration.

To obtain the fixed order of operation, the button 98, as described below, is initially restricted from movement. In addition, the dose knob 86 and the sleeve 36 are provided with the protrusions 82 and the notches 84 described above. In this manner, a dose must be initially set to permit movement of the sleeve 36. Thus, dose setting is required prior to activation of autoreconstitution.

As shown in FIG. 2, the button 98 is preferably located in a first state in proximity to the cross-piece 22 which thus limits distal advancement of the button 98. With this arrangement, the stem 96 cannot be advanced. A secondary spring 106 is disposed to urge the button 98 away from the body 12, e.g., being disposed between the cross-piece 22 and the button 98, with a second releasable retainer 108 releasably retaining the button 98 in the first state against force of movement of the secondary spring 106.

The second releasable retainer 108 includes at least one catch 110 extending from the stem 96 disposed to interferingly engage the cross-piece 22 and retain the button 98 in the first state. Rotation of the stem 96 causes the catch 110 to align with slot 111 (FIG. 4) in the cross-piece 22 thereby releasing the catch 110 from the cross-piece 22, thus, allowing advancement of the button 98. To obtain rotation of the stem 96, at least one thread 112 may be formed on the stem 96. The first plunger portion 16 may also be provided with at least one thread 114 formed to threadedly cooperate with the thread 112. With sufficient relative movement between the first plunger portion 16 and the stem 96, the threads 112, 114 threadedly engage. With the first plunger portion 16 being non-rotatably held by the body 12, the threaded engagement causes the stem 96 to rotate. With rotation, the catch 110 becomes clear of the cross-piece 22, and the button 98 advances proximally away from the body 12 under force of movement of the spring 20. Lips 116 may be formed on the cross-piece 22 and/or the stem 96 to limit proximal movement of the button 98. The button 98 is moved to a ready state where depression of the button 98 results in distal advancement of the stem 96. The extent of permissible movement of the button 98 defines the maximum stroke of the stem 96.

The button 98 is preferably released to the ready state during the autoreconstitution process. It is further preferred that the button 98 be released upon the secondary distal advancement of the plunger 14 obtained with venting of the reservoir 46. In this manner, the button 98 is released to the ready state with the medical injector 10 being ready for use, the post-reconstitution, needle mounted state shown in FIG. 6. Dose administration, thus, can be made only achievable after dose setting and autoreconstitution.

It is noted that proximal advancement of the button 98 also results in proximal movement of the enlarged head 102. With this arrangement, the stem 96 and the tubular portion 100 should be positioned and configured to account not only for distal advancement of the second plunger portion 18 but also account for proximal movement of the enlarged head 102.

Figure 15:
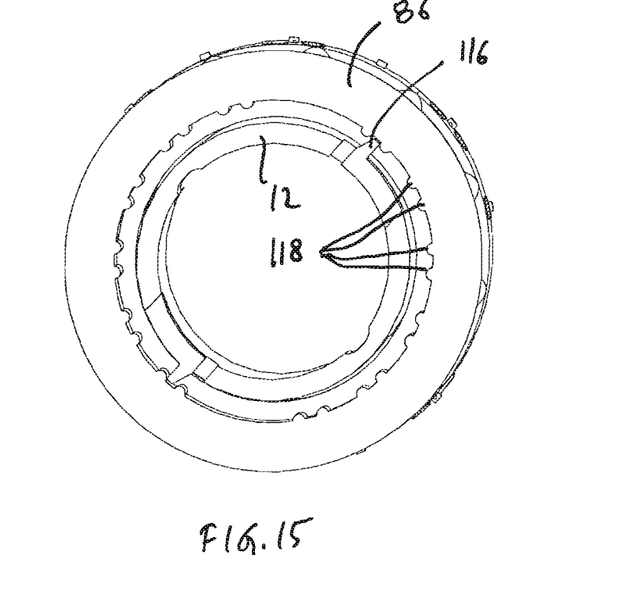
FIG. 15 shows an arrangement for releasably retaining the dose knob in selected positions.

It is preferred that the dose knob 86 be releasably retained in positions corresponding to the various dose settings. In this manner, it is preferred that once a dose has been set, there is no inadvertent rotation of the dose knob 86, thus avoiding that an improper of the abutment surfaces 88 engage the tabs 92. Such an arrangement is disclosed in U.S. Pat. No. 6,793,646. As shown in U.S. Pat. No. 6,793,646, with reference to FIG. 15, one or more locking tabs 116 may be formed on the body 12 which are selectively engageable with one or more ratchet teeth 118 formed on the dose knob 86. The ratchet teeth 118 may be circumferentially spaced apart and positioned to represent dose settings corresponding to the abutment surfaces 88. The tabs 116 nest in between the ratchet teeth 118 at given radial positions corresponding to different dose sizes. With turning of the dose knob 86, the tabs 116 are caused to by-pass the ratchet teeth 118. The ratchet teeth 118 maintain the radial position of the dose knob 86.

What is claimed is:

1. A medical injector comprising:
   a body, said body including a cross-piece at a proximal end thereof;
   a displaceable plunger disposed in said body;
   a spring disposed between the cross-piece and said plunger, said spring configured to cooperate with the cross-piece to advance said plunger;
   a releasable retainer including one or more deflectable locking arms, at least one of said locking arms including a detent having a portion directly and interferingly engaging said plunger to retain said plunger within said body in a first state against force of said spring; and
   a sleeve disposed on, and located exteriorly of, said body, said sleeve including one or more activation surfaces having a ramped portion, said sleeve being slidable relative to said body,
   wherein sliding movement of said sleeve over a predetermined extent relative to said releasable retainer causes said ramped portion of said one or more activation surfaces to directly engage said portion of said detent engaging and retaining said plunger and to deflect the one or more locking arms in an outward direction to release said plunger, wherein the spring cooperates with the cross-piece to advance the plunger.

2. A medical injector as in claim 1, further comprising a dose knob, wherein, in an initial state, said dose knob prevents movement of said sleeve relative to said body.

3. A medical injector as in claim 1, further comprising a reservoir disposed in said body formed to accommodate a medicament.

4. A medical injector as in claim 3, wherein the sliding movement of said sleeve over a predetermined extent which results in said releasable retainer releasing said plunger is also relative to said reservoir.

5. The medical injector of claim 1, wherein said sleeve is separate from and exterior to said plunger.

6. A medical injector comprising:
   a body having a cross-piece with a slot formed therein;
   a displaceable plunger disposed in said body, said plunger having at least one thread formed thereon;
   a stem disposed in said body, said stem having at least one thread formed thereon;
   a button fixed to said stem;
   a spring disposed to advance said button away from said body; and
   a releasable retainer for releasably retaining said button against force of said spring, said releasable retainer comprising at least one catch,
   wherein, said button being retained against force of said spring by said at least one catch interferingly engaging said cross-piece of said body, and
   wherein, said plunger and said stem being configured such that, upon a predetermined extent of relative movement between said plunger and said stem, said thread of said plunger threadably engages said thread of said stem such that said stem rotates, rotation of said stem causing said at least one catch to align with said slot to release said button thereby allowing said spring to advance said button.

7. A medical injector comprising:
   a body having a cross-piece with a slot formed therein;
   a displaceable plunger disposed in said body, said plunger having at least one thread formed thereon;
   a spring disposed to advance said plunger;
   a stem disposed in said body, said stem having at least one thread formed thereon;
   a button fixed to said stem;
   a secondary spring disposed to advance said button away from said body;

a first releasable retainer for retaining said plunger in a first state against force of said spring;

a sleeve disposed on, and located exteriorly of, said body, said sleeve being slidable relative to said body; and a second releasable retainer for releasably retaining said button against force of said secondary spring, said second releasable retainer comprising at least one catch, wherein said button being retained against force of said secondary spring by said at least one catch interferingly engaging said cross-piece of said body, wherein sliding movement of said sleeve over a predetermined extent relative to said first releasable retainer results in said first releasable retainer releasing said plunger thereby allowing said spring to advance said plunger, wherein upon a predetermined extent of relative movement between said plunger and said stem, said thread of said plunger threadably engages said thread of said stem such that said stem rotates, rotation of said stem causing said second releasable retainer to release said button thereby allowing said secondary spring to advance said button, and wherein said rotation of said stem causes said at least one catch to align with said slot to release said button.

8. A medical injector as in claim 7, further comprising a dose knob, wherein, in an initial state, said dose knob prevents movement of said sleeve relative to said body.

* * * * *